(12) United States Patent
Hahn et al.

(10) Patent No.: US 6,174,683 B1
(45) Date of Patent: Jan. 16, 2001

(54) METHOD OF MAKING BIOCHIPS AND THE BIOCHIPS RESULTING THEREFROM

(75) Inventors: Soonkap Hahn, San Clemente; Roberto Fagnani, La Jolla, both of CA (US)

(73) Assignee: Biocept, Inc., Carlsbad, CA (US)

( * ) Notice: Under 35 U.S.C. 154(b), the term of this patent shall be extended for 0 days.

(21) Appl. No.: 09/299,831

(22) Filed: Apr. 26, 1999

(51) Int. Cl.$^7$ .................................................. C12Q 1/68
(52) U.S. Cl. ......................... 435/6; 435/91.1; 435/91.2; 436/518; 436/528; 260/77.5 AM; 260/2.5 AD; 260/2.5 AY; 260/77.5 AP
(58) Field of Search ........................... 435/6, 91.1, 91.2; 436/518, 528; 260/77.5 AM, 2.5 AD, 2.5 AY, 77.5 AP (56) References Cited

U.S. PATENT DOCUMENTS

| | | | |
|---|---|---|---|
| 3,939,123 | 2/1976 | Matthews et al. | 260/77.5 AM |
| 4,110,286 | 8/1978 | Vandegaer et al. | 260/29.2 TN |
| 5,143,854 | 9/1992 | Pirrung et al. | 436/518 |
| 5,552,270 | 9/1996 | Khrapko et al. | 435/6 |
| 5,736,257 | 4/1998 | Conrad et al. | 428/474.4 |
| 5,741,700 | 4/1998 | Ershov et al. | 435/287.1 |
| 5,744,305 | 4/1998 | Fodor et al. | 435/6 |
| 5,756,050 | 5/1998 | Erahow et al. | 422/100 |
| 5,770,721 | 6/1998 | Ershov et al. | 536/25.3 |
| 5,837,832 | 11/1998 | Chee et al. | 536/22.1 |
| 5,847,019 | 12/1998 | Conrad et al. | 522/2 |

*Primary Examiner*—Kenneth R. Horlick
*Assistant Examiner*—Janell E. Taylor
(74) *Attorney, Agent, or Firm*—Fitch, Even, Tabin & Flannery (57) ABSTRACT

Methods for preparing a biochip are provided herein wherein the biomolecular probe to be used with the biochip is alternatively bound to a hydrogel prepolymer prior to or simultaneously with polymerization of the prepolymer. In particularly preferred embodiments, a polyurethane-based hydrogel prepolymer is derivatized with an organic solvent soluble biomolecule, such as a peptide nucleic acid probe in aprotic, organic solvent. Following derivatization of the prepolymer, an aqueous solution, for example sodium bicarbonate, preferably buffered to a pH of about 7.2 to about 9.5, is added to the derivatized prepolymer solution to initiate polymerization of the hydrogel. Alternatively, a water soluble biomolecule, such as DNA or other oligonucleotide, is prepared in an aqueous solution and added to the polyurethane-based hydrogel prepolymer such that derivatization and polymerization occur, essentially, simultaneously. While the hydrogel is polymerizing, it is microspotted onto a solid substrate, preferably a silanated glass substrate, to which the hydrogel microdroplet becomes covalently bound. Most preferably the hydrogel microdroplets are at least about 30 μm thick, for example about 50 μm to about 100 μm thick. The resulting biochips are particularly useful for gene discovery, gene characterization, functional gene analysis and related studies.

41 Claims, 4 Drawing Sheets

Continuation of polymerization until all isocyanates are consumed.

Swelling ratio = (Total weight of hydrogel) / (Weight of prepolymer)

FIG. 3

Spot 1  2  3  4

FIG. 4

METHOD OF MAKING BIOCHIPS AND THE BIOCHIPS RESULTING THEREFROM

BACKGROUND OF THE INVENTION

The present invention relates to new methods of making biochips and the biochips resulting therefrom. In particular, the new method described herein provides for rapid, simple and cost effective construction of biochips by employing polyurethane-based hydrogels to immobilize biomolecular probes on the substrate. In particular, both organic solvent soluble biomolecules, like peptide nucleic acids (PNAs), and water soluble biomolecules, like DNA, RNA and other oligonucleotides, are easily and efficiently bound to the hydrophilic polymer either before or during polymerization thereof. In addition to the improved method of making the biochips described herein, the biochips themselves have improved characteristics including superior stability providing a much improved shelf-life and greater flexibility in use. For example, the biochips of the present invention are useful for gene discovery, gene characterization, functional gene studies, screening for biological activity and related studies.

Agents that selectively bind to DNA or RNA are of significant interest to molecular biology and medicinal chemistry as they may be developed into gene-targeted drugs for diagnostic and therapeutic applications and may be used as tools for sequence-specific modification of DNA. Additionally, such reagents may be used as tools for determining gene sequences and for functional gene analyses. Peptide nucleic acids (PNAs) are a recently developed class of oligonucleotide mimics wherein the entire deoxyribose phosphate backbone has been replaced by a chemically different, structurally homomorphous backbone composed of (2-aminoethyl) glycine units. Despite this dramatic change in chemical makeup, PNAs recognize complimentary DNA and RNA by Watson-Crick base pairing. Furthermore, PNAs have been shown to have numerous advantages over DNA and RNA oligomers. For example, PNAs lack 3' to 5' polarity and thus can bind in either a parallel or an anti-parallel orientation to DNA or RNA. (Egholm, M. et al., *Nature* 365:566, 1993). Another advantage to PNAs is that their selective hybridization to DNA is less tolerant of base pair mismatches than DNA—DNA hybridization. Thus, PNAs are becoming a very useful tool in the study of genes.

Until recently, the processes of gene discovery, characterization and functional gene analysis have been difficult and costly and have required tremendous amounts of time. However, within about the last ten years, methods of isolating arrays of biomolecules on various supports, referred to as biochips, have been developed and have been employed in DNA synthesis, sequencing, mutation studies, gene expression analysis and gene discovery. Generally the biochips are micro matrices (i.e., micro arrays) of molecules bound to a substrate, either directly or through a linking group or, more recently, by way of a gel layer. Most biochips are designed to facilitate synthesis of biomolecules at known locations on a substrate. For example, one such biochip employs light and a series of photo-lithographic masks to activate specific sites on a substrate, such as glass, in order to selectively bind nucleic acids thereto and, subsequently, to attach additional nucleic acids to form known oligonucleotides at the desired locations. This process of using light and photolithographic masks to activate specific sites on a substrate is similar to the processes used in production of the microelectronic semi-conductor chip. Unfortunately, these first generation biochips are very expensive to produce, requiring capital investments in the neighborhood of 2 to 4 million dollars. Furthermore, this synthesis method of forming oligonucleotides in a single layer on a substrate results in a low sensitivity biochip requiring an expensive laser confocal fluorescence microscope for adequate detection of DNA specifically hybridized to the chip. See, for example, U.S. Pat. No. 5,744,305, issued to Fodor, et al. on Apr. 28, 1998 (hereinafter, the '305 patent), which provides an example of the use of photolabile protecting groups and photolithography to create arrays of materials attached to a substrate. The '305 patent, which is hereby incorporated by reference, in its entirety, describes a synthetic strategy for the creation of large scale chemical diversity wherein a substrate, such as glass, is derivatized, either directly or by addition of a linker molecule, to include an amino group blocked with a photolabile protecting group. Masking techniques are then employed to permit selective deprotection of the photolabile groups within a specified, known location on the substrate. The deprotected region is then reacted with a "building block" molecule, for example an oligonucleotide, also containing a photolabile protecting group, such that the building block molecule is covalently bound to the active group at the surface of the substrate (or linker). This process is then repeated using the masks to direct synthesis of polymers, for example peptides, of specific, known sequences at specific, predefined locations on the substrate.

The synthetic strategies described in the '305 patent contemplate providing from about 10 up to about $10^8$ different sequences on a single substrate. Additionally, it is stated that the predefined regions on the substrate, wherein individual polymers are to be synthesized, are from about $10^{-10}$ cm$^2$ to about 1 cm$^2$. While the examples presented in the '305 patent primarily involve synthesis of peptides or nucleotides, it is stated that the same techniques may also be employed in the synthesis of other polymers. Similarly, various linker groups, preferably inactive or inert, for linking the synthesized polymer to the substrate are discussed in the '305 patent, as are various protecting groups for protecting an active site on the monomers which protecting groups may be selectively removed for directed synthesis of the polymer. Also discussed in some detail in the '305 patent is a binary masking technique utilized in one embodiment for directed synthesis of the array. Unfortunately, the strategies described in the '305 patent suffer from many of the same disadvantages as other prior art methods and apparatus. The arrays are expensive to manufacture and use, require multiple steps and lengthy incubation/washing times during manufacture and, significantly, permit synthesis in only a single layer.

In view of the low sensitivity of these first generation biochips, second generation biochips have been developed.

One example of a second generation biochip is described in U.S. Pat. No. 5,736,257 (hereinafter the '257 patent), issued to Conrad, et al., on Apr. 7, 1998, and U.S. Pat. No. 5,847,019, issued to Conrad, et al. on Dec. 8, 1998 (hereinafter, the '019 patent), both of which patent are hereby incorporated by reference, in their entirety. The '257 and '019 patents describe a process of synthesizing a biochip comprising providing a substrate, such as glass, having surface hydroxyl groups; reacting the substrate surface hydroxyl groups with silanes to bind a molecular layer of vinyl groups upon the substrate; placing an acrylaimide compound on the molecular layer, which acrylamide compound can participate in a free radical polymerization reaction to make a polymerized network layer bound to the molecular layer; photo-activating the polymerized network layer to make a patterned photo-activated polymerized network; and placing upon the photo-activated polymerized network layer, for example by synthesis thereon, one or more similar or dissimilar biomolecules to bind to the patterned photo-activated polymerized network layer.

The biochips disclosed in the '257 and '019 patents are somewhat similar to the first generation biochips of Fodor, et al. in that they employ photolithographic techniques to direct binding (or synthesis) of biomolecules to an array. However, in contrast to the first generation biochips, the biochips of the '257 and '019 patents employ a polyacrylamide network on top of a molecular layer of vinyl groups, thereby giving a third dimension to the gel cells. Still, as will be readily appreciated by those of skill in the art, production of biochips in accordance with the disclosures of the '257 and '019 patents is not only expensive but also time consuming.

U.S. Pat. No. 5,552,270 (hereinafter the '270 patent), issued to Khrapko, et al., on Sep. 3, 1996, describes another second generation biochip. The '270 patent, hereby incorporated by reference in its entirety, describes a biochip comprising a solid support and a matrix, including an array of oligonucleotides at desired lengths, the matrix being attached to the support by means of a gel layer having a thickness of no more than 30 $\mu$m. The gel layer described in the '270 patent preferably consists of a set of spaced "dots", according to the number of matrix elements. In contrast to the single layer formats described in the '257 and '305 patents, the gel layer of the '270 patent provides for a three-dimensional attachment of oligonucleotides to the substrate at a capacity therefore exceeding the capacity of the mono-molecular layer of the first generation biochips. This second generation biochip employs a polyacrylamide gel sandwiched between two glass slides that are spaced from one another with spacers no more than 30 $\mu$m thick. Following polymerization of the polyacrylamide gel, one of the slides is removed and the gel-coated lower slide is dried and part of the gel is removed, for example, mechanically, so that the gel portions are separated by interstices, generally of not more than 30 $\mu$m, that remain on the slide surface. In an alternative embodiment described in U.S. Pat. No. 5,770,721 (hereinafter the '721 patent), issued to Ershov, et al., on Jun. 23, 1998, the gel portions to be removed from the slide are removed using a laser. The '721 patent is also hereby incorporated by reference in its entirety for all purposes.

Even these second generation biochips, however, continue to have significant disadvantages. One disadvantage is that the polyacrylamide gel used to form the gel matrix is susceptible to evaporation of water, therefore, the chip must be covered with a non-volatile oil during storage, requiring additional washing with organic solvent, such as chloroform or ethanol, before use for hybridization experiments and reducing the shelf-life of the biochip. Another significant disadvantage to these second generation biochips is cost. Although they do provide increased detection sensitivity, as compared with the first generation biochips, the overall manufacturing cost of this three-dimensional polyacrylamide biochip is still very high due to the complex processes required to produce the chip. In particular, production of this biochip requires lengthy and cumbersome multi-step processing including; polymerization and binding to the surface of the glass substrate; mechanical or laser cutting to form micro-squares of gel matrix on the substrate; an activation step using hydrazines; followed by reaction with the oligonucleotides. Due to the inherent polymerization process of polyacrylamide gels, these steps must be performed independently. Thus, the total time required to produce a single biochip by this method is at least about 24 to 48 hours. Furthermore, after each step, thorough washings and/or other special cares must be taken before the next step may be begun. For example, the oligonucleotide derivatization step requires a long incubation period, such as twenty-four to forty-eight hours. Still another significant disadvantage to the second generation biochips lies in the fact that the reaction of the oligonucleotides with the hydrazine groups forms unstable morpholine derivatives resulting in a very short shelf half-life for the biochip of approximately thirty-six hours at room temperature. Thus, there is a significant need in the industry for a simple, cost effective, rapid method for constructing a reliable multi-functional biochip having a reasonably long shelf-life that may be used in gene discovery, gene characterization, functional gene analysis and related studies.

SUMARY OF THE INVENTION

The present invention provides a rapid, simple, cost effective method for construction of an improved biochip and an improved biochip resulting therefrom. For example, the method described herein allows for binding of biomolecular probes prior to or simultaneously with polymerization of the gel, thereby permitting a simple, one or two step process for production of the biochip. Thus, what has heretofore required multiple steps, multiple washings, and lengthy reaction times, can now be performed in essentially one or two steps. Further provided herein are improved biochips having increased sensitivity, superior stability, both in use and with respect to shelf-life, and improved cost effectiveness.

In a most preferred embodiment described herein, the biochip is formed by dispensing optically transparent microdroplets of polyurethane-based hydrogel, having biomolecular probes covalently attached thereto, on to a substrate. In particular, in aspect, provided herein is a method of preparing a polyurethane-based hydrogel biochip having a biomolecule immobilized thereon, the method comprising providing an organic solvent solution of a polyurethane-based hydrogel prepolymer; providing a solution of the biomolecule to be immobilized thereon; covalently binding the biomolecule to the polyurethane-based hydrogel prepolymer; initiating polymerization of the polyurethane-based hydrogel prepolymer; and dispensing the polymerizing polyurethane-based hydrogel prepolymer onto a solid substrate, such that said solution is covalently bound to said substrate. In preferred embodiments described herein, the polyurethane-based hydrogel has active isocyanate groups thereon, which isocyanates participate in the covalent binding of the biomolecular probe to the hydrogel prepolymer as well as participate in polymerization of the hydrogel.

In another aspect, provided herein is a polyurethane-based hydrogel biochip comprising a solid, transparent substrate having active amines on its top surface, such as a glass substrate treated with silane; a polyurethane-based hydrogel cell covalently bound to the top surface of the substrate, wherein the hydrogel cell is at least about 30 $\mu$m thick, and more preferably about 50 $\mu$m to about 100 $\mu$m thick; and a biomolecular probe covalently bound to and within the hydrogel cell. Again, most preferably the polyurethane-based hydrogel contains active isocyanate groups, preferably about 0.8 meq/g or less, through which the biomolecular probe is attached to the gel. Where DNA or another oligonucleotide is used as the biomolecular probe, the DNA is preferably derivatized, for example with a diamine, such as hexane diamine, to include an active amine for reaction with the isocyanates of the hydrogel prepolymer.

In a still further aspect the present invention includes a hybridization assay, employing the biochips described herein. In particular, the hybridization assay comprises providing a polyurethane-based hydrogel biochip, wherein the biochip comprises a transparent substrate having at least two polyurethane-based hydrogel cells covalently bound thereto, each cell having a thickness of at least about 30 $\mu$m, and wherein at least one hydrogel cell further includes a biomolecular probe covalently bound thereto; contacting the hydrogel biochip with an analyte solution, containing a target biomolecule, under hybridization conditions; washing the hydrogel biochip under conditions that remove most non-specifically bound and unbound target biomolecule; and detecting the bound target biomolecule. In preferred embodiments, the target biomolecule is labeled with a molecular tag, such as a fluorescent marker. Following hybridization of the target biomolecule with the gel-immobilized, biomolecular probe and washing of the hydrogel to remove non-specifically bound and unbound target biomolecule, the hydrogel biochip is illuminated with a fluoroscope to fluoresce the bound target biomolecule and thereby identify complimentary probes.

Preferably, of course, each microdroplet of hydrogel contains a different biomolecular probe, thereby permitting screening of large numbers of biomolecular probes in a single reaction. In one preferred embodiment, the biomolecular probes used in constructing the biochips described herein are peptide nucleic acid probes which provide superior screening functions as compared to traditional DNA and/or RNA oligonucleotides. Alternatively, other biomolecular probes such as DNA, RNA or other oligonucleotide probes are used in conjunction with the polyurethane-based gel matrix, rather than PNAs.

DETAILED DESCRIPTION OF THE PREFERRED EMBODIMENT

In order to provide a three-dimensional gel matrix useful in producing a biochip, the polymer chosen to comprise the gel matrix must have a number of desirable properties. These properties include, for example: 1) adequate pore size and high water content to permit diffusion of molecules in and out of the matrix; 2) the ability to bind to the surface of a substrate, such as glass; 3) sufficient transparency, in its fully polymerized state, to reduce optical interference with fluorescent tags; and 4) sufficient structural integrity, when fully polymerized, to withstand the forces encountered during use. Furthermore, the selected gel is preferably easy to produce and use.

Hydrogels are a class of polymers that meet with these criteria. Hydrogels are hydrophilic network polymers which are glassy in the dehydrated state and swollen in the presence of water to form an elastic gel. The polyacrylamide gel matrices described in Ershov, et al., are hydrogels having a water content, at equilibrium, of about 95% to 97%, providing favorable diffuseability for target molecules such as DNA's. See for example, U.S. Pat. Nos. 5,741,700, 5,770,721 and 5,756,050, issued to Ershov, et al., on Apr. 21, 1998, Jun. 23, 1998 and May 26, 1998, respectively and U.S. Pat. No. 5,552,270, issued to Khrapko, et al., issued Sep. 3, 1996, each of which patents is hereby incorporated by reference, in its entirety. The polyacrylamide-based biochip described by Ershov, et al., is based upon the polymerization of acrylamide monomers by a free radical initiation or ultra-violet radiation process. Additionally, as previously indicated this polyacrylamide-based gel biochip is constructed in a multi-step process that is lengthy and labor intensive.

In contrast to the polyacrylamide gel system of Ershov, et al., the inventors herein have discovered that polyurethane-based hydrogels lack most of the disadvantages of the polyacrylamide-based gels while possessing a number of important advantages over the prior art. Polyurethane-based hydrogel polymers are well known and have been used extensively in the production of absorbent materials such as surgical dressings, diapers, bed pads, catamenials, and the like. The polyurethane-based hydrogels used in these materials advantageously absorb large quantities of liquid quickly and in a relatively uniform manner such that the basic overall shape of the gel material is maintained. Further, the moisture absorbed by these materials is retained in the absorbent material even under an applied pressure. Such polyurethane-based hydrogels are described, for example, in U.S. Pat. Nos. 3,939,123, issued to Mathews, et al., Feb. 17, 1976 and 4,110,286, issued to Vandegaer, et al., Aug. 29, 1978, which patents are hereby incorporated by reference, in their entirety. While the polyurethane-based hydrogels, as described for example in U.S. Pat. Nos. 3,939,123 and 4,110,286, have been extensively used as surface coatings and have been used to form flexible or rigid foams, the use of this material to form a three-dimensional matrix having chemical compounds of interest attached thereto, to the inventor's knowledge, has heretofore not been contemplated or described.

In a preferred embodiment, the biochip of the present invention uses a polyurethane hydrogel based on a prepolymer of polyethyleneoxide, or a copolymer of polyethyleneoxide and polypropyleneoxide, capped with water-active diisocyanates and lightly cross-linked with polyols such that the quantity of isocyanates present is predictable for example is at most about 0.8 meq/g. Frequently used diisocyanates include aromatic-based diisocyanates, such as toluene diisocyanate or methylene diphenyl-isocyanate, as well as aliphatic diisocyanates, such as isophorone diisocyanate. The polymerization of the prepolymer, which may be preformulated in water-miscible organic solvent, takes place simply by the addition of water. This is a distinct advantage over the hydrogel-based biochips previously known, wherein ultraviolet radiation or similarly severe reaction conditions are necessary to initiate polymerization. Not only is the water-activated polymerization system of the present invention safer, less expensive and easier to work with, but it allows for derivatization of the pre-polymer with the appropriate biomolecular probe prior to or simultaneously with polymerization.

In one embodiment described herein, prior to polymerization, the hydrogel is derivatized with organic biomolecules soluble in organic solvent using a simple two to three-minute reaction between the biomolecules, preferably peptide nucleic acids which have been previously derivatized with amine, and the isocyanates of the prepolymer. In order to prevent premature polymerization of the hydrogel in the present embodiment, the derivatization reaction is carried out in aprotic water-miscible organic solvent such as, for example, dimethylformamide (DMF), N-methyl-2-pyrrolidinone (NMP), acetone, acetonitrile or others. Thus, prior to swelling of the hydrogel or dispensing of the hydrogel onto the substrate, biomolecular probes are covalently bound to the polyurethane-based prepolymer gel. Following such derivatization, the addition of water initiates polymerization, resulting in biomolecular-derivatized hydrogels, for example, PNA-derivatized hydrogels.

In this embodiment, the use and presence of aprotic solvent in the derivatization of the hydrogel serves at least four purposes. First, it helps generate a homogeneous solution of the prepolymer in water. Second, it serves to separate the derivatization step from the polymerization step, whereby almost quantitative yield of biomolecule derivatization to the hydrogel can be achieved. Third, it serves to slow down the generation of carbon dioxide during the polymerization step and effervesce carbon dioxide efficiently by lowering the viscosity of the polymerizing mixture. In the polymerization of the polyurethane-based hydrogels preferred herein, carbon dioxide is generated by the reaction of water with the isocyanate groups of the hydrogel prepolymer. This reaction scheme is illustrated, for example in FIGS. 1 and 2. Controlling the generation of carbon dioxide and its escape from the gel are critical to providing an effective, useful biochip. If the polymerization occurs too quickly and in a highly viscous mixture, the carbon dioxide generated thereby is not able to escape and becomes trapped within the gel resulting in a discrete foam matrix. While such is not a problem when polyurethane-based hydrogels are used in diapers, bed pads or similar known uses, continuum of the gel matrix is critical in its use in biochips in order to permit accurate and efficient detection of fluorescence indicative of successful hybridization.

A fourth and final advantage to the use of an aprotic solvent to derivatize the hydrogel in the present embodiment is that its presence enhances the optical transparency of the hydrogel by reducing precipitation of the prepolymer. It has been discovered by the inventor that the ratio of aprotic solvent to water must be higher than about 0.25 to allow sufficiently slow polymerization of the gel and, therefore, slow generation of $C_2$, to result in a continuous and transparent gel matrix, in accordance with the present invention. The total time required for derivatization and polymerization of the hydrogel is most preferably about thirty minutes. This is in stark contrast to the twenty-four to forty-eight hours required for preparation of polyacrylamide based biochips. Furthermore, the quantity of biomolecule, PNA, for example bound to the prepolymer may easily be adjusted by simply varying the amount of biomolecule added to the reaction (for example, where PNA is the biomolecule to be bound to the gel, from about 10 fmol up to about 1 pmol of PNA may be used), thereby permitting greater control over the concentration of capture probes within each hydrogel microdroplet.

In this preferred embodiment, the hydrogel is derivatized with PNA then deposited onto the solid substrate, after initiation and before completion of polymerization thereof. This may be accomplished by any convenient method, for example by use of a microspotting machine. The gel is preferably deposited to form an array of microdroplets. It will be appreciated by those of skill in the art that the substrate surface will generally have to be derivatized prior to addition of the hydrogel, for example, in preferred embodiments, where glass is used as the substrate, the glass is derivatized with amine prior to deposit of the polymer-izing hydrogel onto its surface. Thus, the polymerizing hydrogel, derivatized with a biomolecular capture probes such as PNAs or DNAs, is able to bind to the substrate as it is deposited onto the derivatized glass substrate, via reaction of active isocyanate groups within the prepolymer with the amines located on the surface of the glass thereby providing covalent attachment of the hydrogel to the substrate. Most advantageously, all reactions involved in this system, namely (1) the derivatization of hydrogel prepolymer with the biomolecular probe, (2) the polymerization of hydrogel and (3) the binding of derivatized hydrogel to the substrate surface, involve the formation of strong urea bonds. These provide mechanical integrity to the microdroplet array, and significantly increase the half-life of the biochip as compared with the polyacrylamide-based biochip described in the prior art.

In preferred embodiments described herein, the hydrogel droplets, once polymerized on the substrate, are at least about 30 $\mu$m thick, more preferably at least about 50 $\mu$m thick and most preferably between about 50 $\mu$m and 100 $\mu$m thick. Furthermore, the droplets will be generally elliptical in shape, as opposed to the square gel cells previously known. It will be readily appreciated that the larger size of the gel droplets (or cells) of the present invention permit a significant increase in the quantity of biomolecular probe immobilized therein, thereby increasing the sensitivity of the biochip and facilitating its use.

In alternative embodiments contemplated herein, water soluble biomolecules, such as DNA or other oligonucleotides, are bound to the hydrogel instead of the organic soluble biomolecules previously described. In these embodiments, it is not possible to first derivatize the hydrogel prepolymer and then initiate polymerization. However, the inventor herein has discovered that the polyurethane-based hydrogels may be derivatized and polymerized in a single reaction and that such reaction may be adequately controlled to provide a derivatized hydrogel having a relatively predictable quantity of water soluble biomolecular probe attached thereto. In particular, in these embodiments, the hydrogel prepolymer is first dissolved in an organic solvent. The DNA or other water-soluble biomolecule, in aqueous buffer solution, is then added to the prepolymer in a quantity and under appropriate conditions such that the hydrogel is both derivatized with the biomolecular probe and is polymerized. As the hydrogel is polymerizing and before the polymerization is complete, it is microspotted onto a suitable substrate, as previously described.

Optimization of Hydrogel Formulation

To be useful in a biochip, a hydrogel must have a number of favorable characteristics. In particular, considerations for determining appropriate hydrogel formulations are: (1) the swelling capacity of the hydrogel; (2) the time required for polymerization; (3) the transparency of the fully polymerized hydrogel; and (4) the strength (i.e., stability) of the fully polymerized hydrogel. Optimization of these characteristics provides an optimum hydrogel. Swelling capacity is an important characteristic of the hydrogel because it reflects the maximum water content. Generally, the higher the water content of the polymerized gel, the faster the diffusion of molecules in and out of the gel. Naturally, where a biochip is concerned, the faster the diffusion of molecules, for example, DNA samples, the more efficient the hybridization reactions. The mathematics of molecular diffusion in simple swelling polymers is based on the following semi-empirical equation (Davis B.K. *Proc. Natl. Acad. Sci. USA* 21:3120, 1974):

$D_p = D_o \exp[-0.05 + (10^{-6} \, M) \, P]$ wherein, $D_p$ = Diffusion coefficient of the specified molecules in the polymer solution $D_o$ = Diffusion coefficient of the specified molecules in pure water M = Molecular weight of the specified molecules P = Percent polymer content Thus, from this equation it can be seen that the higher the water content, the faster the diffusion of molecules in and out of the polymer.

Optimizing the time required for polymerization of the hydrogel is particularly important in the processing of a biochip in accordance with the present invention. Ideally, the time required for polymerization should be long enough to permit dispensing of the polymerizing gel onto the surface of the glass substrate with a microspotting machine before polymerization is complete, and short enough that once dispensed, the hydrogel fully polymerizes shortly thereafter. Based on these requirements, it was determined by the inventors that a hydrogel with a polymerization time of about thirty minutes and with a swelling capacity of about 96% to 97% at equilibrium would be optimal. Various experiments were conducted in order to determine the most appropriate formulations and reaction conditions to provide an optimum hydrogel formulation. These experiments included the evaluation of prepolymer-solvent ratios, solvent types and buffer conditions with respect to both gel transparency and polymerization rate. The results are outlined in the following sections.

I. Evaluation of Prepolymers and Polymer-Water Ratios

In initial experiments, the inventors herein found that prepolymers capped with aromatic polyisocyanates polymerized in 2–3 minutes when treated with deionized water, much too quickly for use in the biochip setting. In contrast, prepolymers capped with aliphatic polyisocyanates took longer than 35 minutes to complete polymerization, under the same conditions. Thus, the prepolymers capped with aliphatic polyisocyanates were selected for further optimization. In particular, prepolymers having an active isocyanate content of at least about 0.3 meq/g were used. In order to optimize the prepolymer-water ratio, varying amounts of prepolymer were dissolved in water and the polymerization time was determined. As shown in Table 1, and as would be expected, polymerization time increased as the proportion of prepolymer in the aqueous solution decreased. For example, the hydrogel resulting from a 5% prepolymer solution polymerized only on the surface, even after 48 hours. In contrast, the prepolymer solution having 10% prepolymer content polymerized in three hours and the 20% solution was fully polymerized within about 35 minutes. From these initial experiments, then, it appeared that a prepolymer solution of about 20% and, in any case, of greater than about 10%, would be preferred for use in the biochips.

TABLE 1

| % prepolymer in aqueous solution | Polymerization time |
|---|---|
| 5% | >48 hours |
| 10% | 3 hours |
| 20% | 35 minutes |

II. Effect of pH on Polymerization

The next step toward optimization of the hydrogel formulation was to determine the effect of pH on the rate of polymerization. Table 2 summarizes examples of results of these experiments.

TABLE 2

| % prepolymer in aqueous solution | pH 7.2 | pH 8.4 |
|---|---|---|
| 5% | 90 minutes | 20 minutes |
| 10% | 17 minutes | 3 minutes |

In these experiments, it was found that 50 mM sodium bicarbonate aqueous buffers at pH 7.2 and 8.4 significantly accelerated the polymerization rate of the hydrogel. Thus, for example, when a 5% prepolymer formulation was used, polymerization time decreased from >48 hours to only 20 minutes at pH 8.4 and to 90 minutes at pH 7.2. Similarly, the 10% prepolymer solution was fully polymerized within 17 minutes at pH 7.2 and within 3 minutes at pH 8.4. Thus, these experiments indicated that by adjusting the pH of the polymerization reaction, a lower prepolymer content, i.e. 5% or 10%, could be used in the hydrogel formulation. However, in addition to polymerization time, the swelling properties of the gel must be considered. While polymerization may occur quickly, the gel is most useful when it has reached the desired water content of at least about 95%, preferably about 96% to 97%. Thus, the swelling characteristics of the different polymer content formulations were also analyzed.

Figure 3:
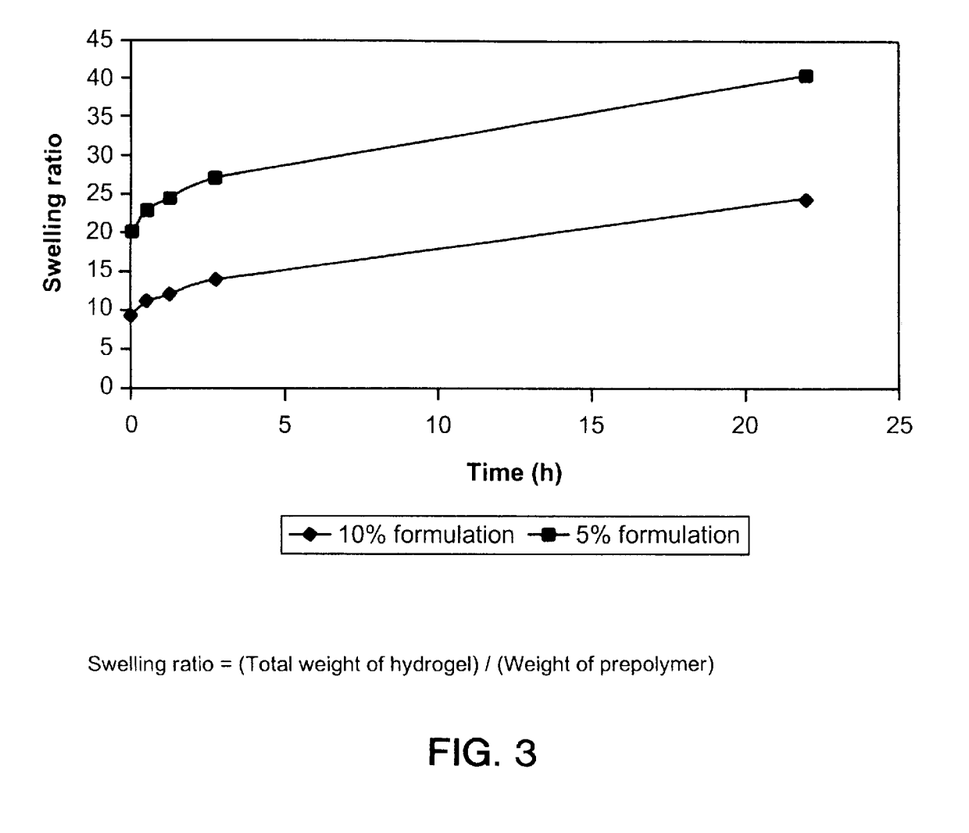
FIG. 3 is a graph illustrating the differences in swelling ratios, over time, of a 10% and 5% solution of hydrogel polymer, in accordance with the present invention.

FIG. 3 is a graph comparing the swelling profiles of a 5% hydrogel formulation and a 10% hydrogel formulation. From these profiles, it can be seen that the hydrogel made using a 10% prepolymer solution required about one day to achieve an optimum water content of 96%. In addition, the volume of hydrogel, when fully swollen, was about twice the volume at just after polymerization, making the structural integrity of this hydrogel difficult to maintain. In contrast, the hydrogel resulting from a 5% prepolymer solution reached 96% water content in about one hour and did so without losing its structural integrity. Thus, based upon both its polymerization rate in basic solution and its swelling profile, the 5% prepolymer solution was selected for still further optimization.

III. Optimizing Transparency of the Hydrogel

A significant disadvantage to hydrogels made from aqueous solutions is they are generally opaque. In order to be useful in a biochip setting, the gel must be transparent, and in particular should be optically transparent so that interference with molecular markers, such as fluorescent tags is minimized. To achieve optical transparency, the hydrogel prepolymer was first dissolved in aprotic organic solvent such as, but not limited to, acetonitrile, acetone, DMF or NMP, and the resulting solution was treated with 50 mM sodium bicarbonate buffer at pH 7.2 or 8.4 to initiate polymerization. Using the preferred 5% polymer solution, the ratio of aprotic solvent to aqueous buffer was adjusted to determine an optimum formulation with respect to polymerization time and optical transparency. Table 3 shows the results of testing of five different hydrogel formulations having various ratios of buffer to aprotic solvent, in this case acetonitrile. Each formulation was tested at a buffered pH of 8.4 and 7.2.

TABLE 3

| Formulation # | Acetonitrile: Buffer | Time to polymerize |
|---|---|---|
| | DI water | |
| control | 0.3 g:0.65 g pH 8.4 buffer | 3 hours |
| 1 | 0.1 g:0.85 g | 45 minutes |
| 2 | 0.2 g:0.75 g | 42 minutes |
| 3 | 0.3 g:0.65 g | 35 minutes |
| 4 | 0.4 g:0.55 g | 35 minutes |
| 5 | 0.5 g:0.45 g pH 7.2 buffer | 32 minutes |
| 6 | 0.1 g:0.85 g | 45 minutes |
| 7 | 0.2 g:0.75 g | 40 minutes |
| 8 | 0.3 g:0.65 g | 30 minutes |
| 9 | 0.4 g:0.55 g | 32 minutes |
| 10 | 0.5 g:0.45 g | 30 minutes |

Each of the tested formulations polymerized within about 30–45 minutes, regardless of the relatively large differences in the ratio of acetonitrile to buffer and varied pH. Optical transparencies of each formula, however, varied with respect to the ratio of organic solvent (acetonitrile) to aqueous buffer (NaHCO$_3$). In particular, optical transparency, which is measured using a charge-coupled device camera combined with filters, as well as visual transparency, improved as the ratio of organic solvent to aqueous buffer increased. Thus, it was determined that hydrogel formulations employing at least about 30% organic solvent (acetonitrile) were preferred.

IV. Comparison of Aprotic Organic Solvents

The next step in optimization of the hydrogel for the biochips of the present invention, was a comparison of aprotic solvents. Experiments similar to those described in Section II were performed using various aprotic solvents, such as DMF, NMP and acetone. While it was assumed these alternative organic solvents would function similarly to acetonitrile, such was not the case. Results of polymerization studies of hydrogel formulations having 30% DMF, NMP or acetone are summarized in Table 4.

TABLE 4

| Solvent | pH of buffer | Polymerization time |
|---|---|---|
| DMF | unbuffered DI water | Did not polymerize |
| | 8.4 | Did not polymerize |
| | 9.15 | 20 minutes |
| | 9.5 | 8 minutes |
| | 10 | Did not polymerize |
| NMP | unbuffered DI water | Did not polymerize |
| | 8.4 | Did not polymerize |
| | 9.15 | Did not polymerize |
| | 9.5 | Did not polymerize |
| | 10 | Did not polymerize |
| Acetone | unbuffered DI water 8.4 | Did not polymerize 30 minutes |

From these experiments, it was discovered that formulations in DMF required a higher pH to polymerize while, under the same conditions, formulations in NMP did not polymerize at all. Formulations in acetone were most similar to acetonitrile formulations in that they required only slightly basic pH to polymerize. Significantly, the hydrogels resulting from DMF or acetone formulations lacked the structural integrity of the hydrogels produced in acetonitrile. Thus, from these optimization studies, acetonitrile was selected as the preferred aprotic solvent for use in the further development of the optimized biochip.

Derivatization of the Hydrogel with a Biomolecular Probe

I. Derivatization with a Peptide Nucleic Acid Probe

A. Optimization of Reaction Conditions

Having optimized the hydrogel formulation with respect to water content, structural integrity, polymerization time, optical transparency and organic solvent, the next step in providing a superior biochip was to derivatize the gel with an appropriate biomolecular probe. As discussed above, in one preferred embodiment, peptide nucleic acid (PNA) probes are used to derivatize the hydrogel. PNAs are more stable than and bind more strongly to DNA than do DNA probes. Thus, PNA probes were generated for use in derivatizing a preferred hydrogel formulation, in accordance with this first embodiment.

Figure 1:
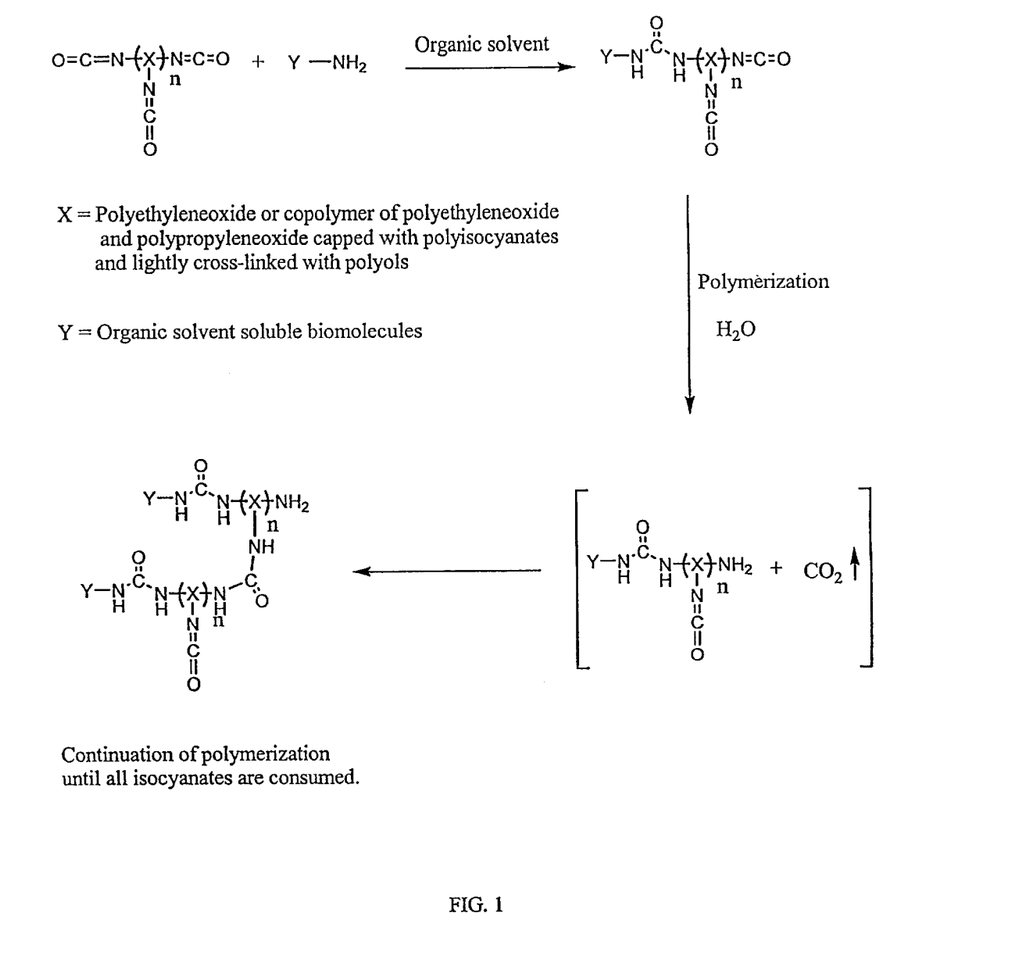
FIG. 1 is a schematic illustrating the reaction of a hydrogel prepolymer with an organic soluble biomolecule followed by polymerization of the hydrogel, in accordance with a preferred embodiment of the present invention.

In order to derivatize the preferred hydrogel formula, the PNAs were first dissolved in acetonitrile, the same preferred aprotic solvent found useful in preparing the hydrogel. Unfortunately, however, it was discovered that PNAs are only minimally soluble in acetonitrile. In order to coax the PNAs into solution, a more polar solvent was selected, namely N-methyl-2-pyrrolidinone (NMP). However, as illustrated above, hydrogel formulations using NMP do not polymerize under the various conditions tested. While it was not clear why the hydrogel formulations containing NMP polymerized differently from those containing acetonitrile, it was thought that a solution containing both NMP and acetonitrile might be capable of optimization to provide both favorable solubility for PNAs and favorable polymerization for the hydrogel. After numerous studies of various acetonitrile/NMP ratios, an optimum formulation was determined, having a solution ratio in the range of 3:1 to 2:1 acetonitrile to NMP and using an aqueous solution of 50 mM sodium bicarbonate to buffer the polymer/PNA solution at pH 8.4 to 9.15. This formulation polymerized in an optimum time of 20–30 minutes. FIG. 1 illustrates, schematically, the reaction of the hydrogel prepolymer with an organic soluble biomolecule, such as, PNA, and the polymerization of the derivatized prepolymer.

B. Effect of PNA Derivatization on Polymerization of the Hydrogel

The next step, in providing a PNA biochip, in accordance with this first preferred embodiment of the present invention, was to evaluate the extent to which the degree of derivatization with PNA affects polymerization of the hydrogel. The preferred hydrogel formulation has an active isocyanate content of at least about 0.3 meq/g, and preferably of about 0.3–0.8 meq/g, in acetonitrile. Experiments were performed wherein different percentages of the active isocyanates were derivatized with a test compound, benzylamine, for five minutes. The derivatized hydrogels were then polymerized by treating with 50 mM sodium bicarbonate buffer at pH 8.4. Derivatization of 10% of the active isocyanates with benzylamine resulted in a polymerized hydrogel having characteristics similar to those of the underivatized, polymerized hydrogel. In contrast, when 20% of the active isocyanates were treated with benzylamine, the resulting formulation did not polymerize, indicating that an insufficient quantity of active isocyanates were available for polymerization after benzylamine derivatization. Thus, it was determined that derivatization of about 10% of the active isocyanates of the gel, was preferred. When 10% of the active isocyanates are derivatized with PNA, it is estimated that about 1 to 2 pmol of PNAs are bound within each about 1 nanoliter droplet of hydrogel.

II. Derivatization with a DNA Probe

In an alternative embodiment contemplated herein, the hydrogel of the present invention is derivatized with a DNA (or similar oligonucleotide) probe. Unlike PNA however, DNA is not soluble in organic solvent. Therefore, where DNA is used as the biomolecular probe, the derivatization and polymerization steps cannot be separated from one another as they can when the derivatization is with PNA. Additionally, of course, unlike PNA, DNA does not have an active amine (or other) group available for binding to the active isocyanates of the polymer. Thus, the DNA preferably is derivatized with an appropriate active group, such as a diamine, prior to reaction with the prepolymer.

As with the previously described embodiment, wherein the hydrogel was derivatized with PNA, the organic solvent and aqueous buffer solution amounts and reaction conditions are selected to optimize the hydrogel polymerization with respect to polymerization time, gel transparency and related characteristics. Thus, a polymer content of about 5% and an organic solvent content of at least about 30% are preferred. Similarly, it is preferred to derivatize less than 20%, for example, about 10% or less, of the active isocyanates of the hydrogel with the DNA probe. Thus, for example, in a referred embodiment, exemplified below, about 2.5% of the active isocyanates of the hydrogel were derivatized with the DNA probe. Additionally, polymerization is preferably accomplished using a basic buffered aqueous solution, most preferably at about pH 7.2 to about 9.5, for example, 8.4 to 9.3.

Figure 2:
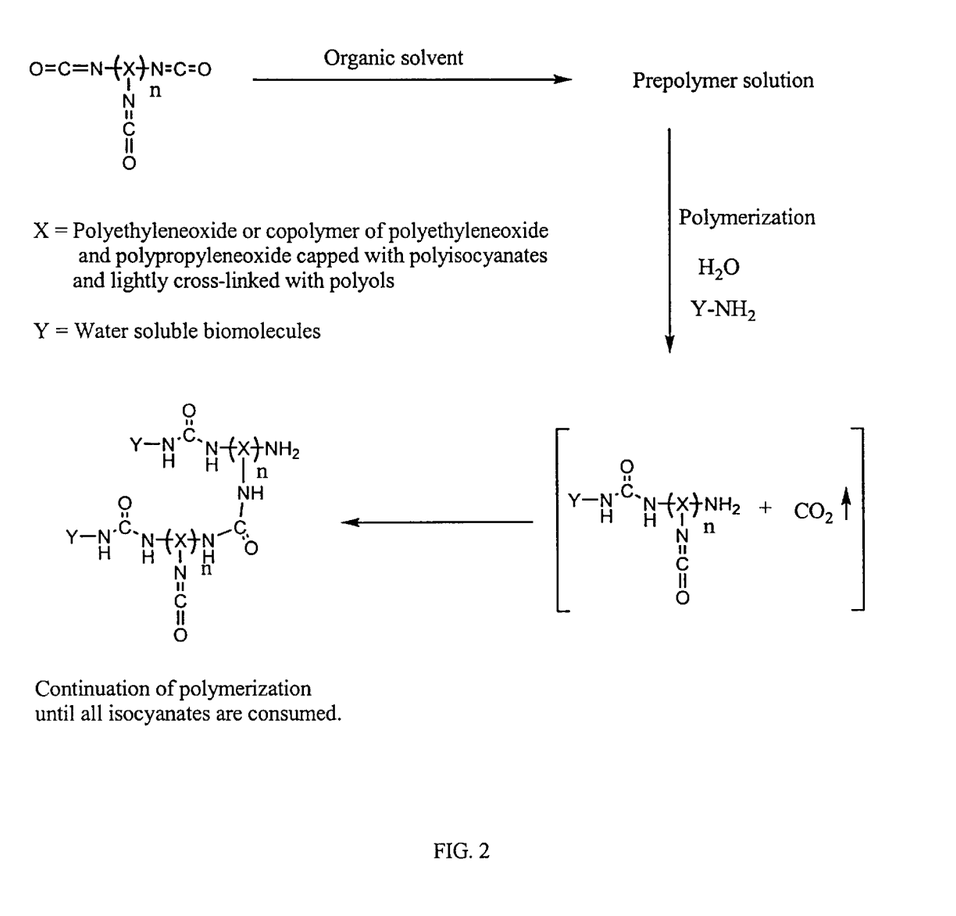
FIG. 2 is a schematic illustrating the reaction of a hydrogel prepolymer with a water soluble biomolecule, such as DNA, during polymerization of the hydrogel.

To prepare the derivatized hydrogel, in accordance with this alternative embodiment, the prepolymer is first dissolved in an organic solvent, for example, acetonitrile, and the derivatized DNA (or other oligonucleotide) probe is prepared in aqueous buffer. The DNA solution is then added to the prepolymer solution with thorough mixing resulting in both derivatization of the gel and initiation of polymerization. It will be readily appreciated by those of skill in the art that this general method of dissolving the polyurethane-based hydrogel in organic solvent and adding thereto the water soluble biomolecular probe in aqueous solution is applicable to numerous water soluble probes in addition to oligonucleotides. FIG. 2 illustrates, schematically, the simultaneous reaction of a water soluble biomolecule, such as DNA, with the hydrogel prepolymer and polymerization of the hydrogel.

Binding of Hydrogel to the Surface of the Substrate

The final step to be considered in optimizing the biochips of the present invention was the step of dispensing the derivatized hydrogel prepolymer formulation onto a suitable substrate, under appropriate conditions to permit covalent binding of the hydrogel to the substrate surface. In preferred embodiments, the substrate selected is transparent, in order to reduce interference with signal detection when the biochip is in use. A most preferred substrate is glass. The surface of the glass substrate is first derivatized with amine, in order to provide active sites for covalent binding of the polymerizing hydrogel. Just prior to dispensing the derivatized hydrogel onto the derivatized glass substrate polymerization is initiated either by addition of aqueous buffer to the derivatized prepolymer, in the case of derivatization with an organic solvent soluble biomolecule, or by addition of aqueous buffer including a water soluble biomolecule. The polymerizing hydrogel is then micro-spotted onto the glass substrate to form an array of microdroplets most preferably having a thickness of more than about 30 $\mu$m.

In preferred embodiments, a 50 mM sodium bicarbonate aqueous buffer solution, pH from about 7.2 to about 9.5, was used to initiate polymerization of the hydrogel. Under these conditions, the preferred hydrogel formulation bound tightly to the surface of the derivatized glass within about 1 to 5 minutes from the initiation of polymerization by the addition of the aqueous buffer. It will be appreciated that, where PNA or other organic solvent soluble probe is used, the derivatized prepolymer need not be used immediately following derivatization, but rather may be set aside or, under proper conditions, even stored prior to initiation of polymerization by addition of aqueous buffer. In contrast, where the prepolymer is derivatized with a water soluble probe, derivatization begins upon addition of the probe to the prepolymer solution and, therefore, the polymerizing hydrogel should be dispensed shortly thereafter.

Advantageously, polyurethane-based hydrogels, as used in accordance with the present invention, polymerize quickly into very stable microdroplets. Preferably, the hydrogel is dispensed onto the substrate such that it forms microdroplets of at least about 30 $\mu$m in height and most preferably about 50 $\mu$m to about 100 $\mu$m in height. In order to optimize consistency between the hydrogel droplets, the polymerizing gel is preferably dispensed using a microspotting or similar automated machine. It will be readily appreciated by those of skill in the art that providing such thick gel droplets, or gel cells, can dramatically increase the sensitivity of the biochip.

In order to prevent over-crosslinking of the polymerizing gel, which can result in an increase in the polymer concentration as water is evaporated from the gel and which may also cause wrinkling in the surface of the gel droplet, the biochip is preferably cured in a humid environment, such as a humidity chamber, and thereafter washed with de-ionized water.

The viscosity and sheathing properties of the polymerizing hydrogel against the glass substrate are important to provide a reasonable and consistent shape of droplets throughout the array. In an ideal situation, the viscosity of the polymerizing hydrogel would increase slowly and in a linear fashion. Unfortunately, however, the viscosity of hydrogels tend to increase exponentially during polymerization. To facilitate a more linear expansion of the hydrogel during polymerization its viscosity was optimized using thickening agents, such as polyethylene glycol, of various molecular weights. The viscosity of the hydrogel during polymerization may be measured, for example with a viscometer, following addition of the thickening agent. From experimentation, it was determined that addition of polyethylene glycol having a molecular weight of about 1,000 up to an amount equal to the weight the prepolymer significantly improved the formulation's viscosity and sheathing properties. Thus, in preferred embodiments contemplated herein, polyethylene glycol or similar thickening agent is added to the hydrogel during polymerization thereof to control the rate of polymerization.

EXAMPLE I

Hybridization Experiment with PNA Chip

A solution of 1 mg PNA (0.3 $\mu$M) having the sequence $NH_2$-CATTGCTCAAAC-$CO_2H$ was prepared in 0.1 g of NMP. Next, a solution of 0.05 g polyurethane prepolymer having an isocyanate content of about 0.5 meq/g (Hypol PreMa G-50 manufactured by Hampshire Chemical Corporation) in 0.2 g acetonitrile was prepared and added to the PNA-NMP solution. The resulting solution was treated with 0.65 g of a 50 mM $NaHCO_3$ solution at pH 8.4. After thorough mixing, a droplet of the resulting solution was manually spotted on a silanated glass slide using a capillary microtube. The droplet polymerized on the surface of the glass in about 15 minutes. As a negative control, a hydrogel droplet containing no PNA was spotted next to the PNA-containing hydrogel droplet.

Figure 4:
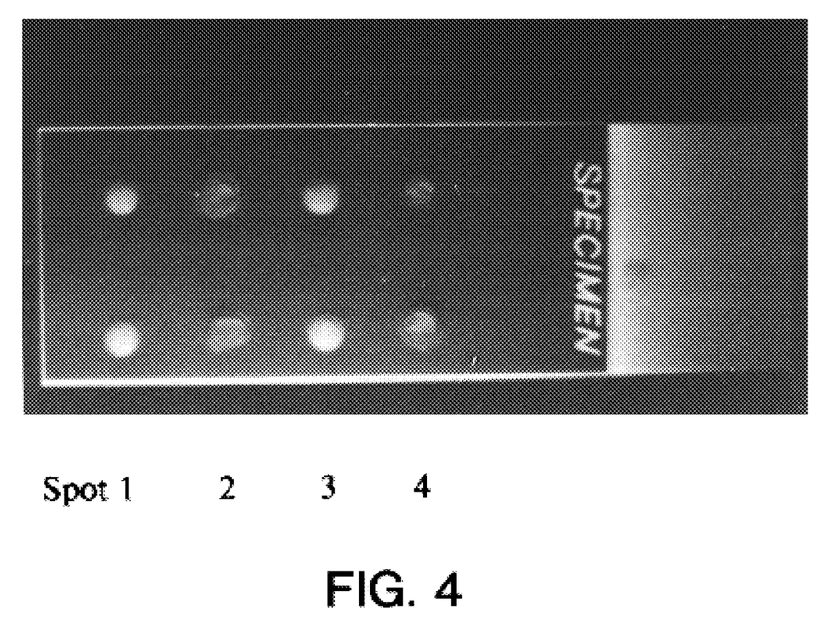
FIG. 4 illustrates the results of a hybridization experiment performed using a hydrogel biochip in accordance with the present invention.

The glass slide, having the hydrogel droplets thereon, was submersed into washing buffer (5 mM sodium phosphate buffer with 0.05% SDS at pH 7.0) for 30 minutes to remove organic solvents and block active sites to prevent non-specific binding of test DNA. Next, the slide was treated with 1 mg of a complementary fluoresrence-labeled DNA, 3'-TAGTAACGAGTTTGCC-5'-Fluorescein, in hybridization buffer containing 600 $\mu$L of 10 mM sodium phosphate buffer with 0.1% SDS at pH 7.0 at room temperature, for 1 hour. Non-specifically bound DNA was removed by washing for two hours in washing buffer. The resulting slide was observed with a hand-held fluorescence detector (Model UVGL-25, UVP), As shown in FIG. 4, the test DNA diffused into the hydrogel microdroplets where it hybridized to the complementary PNA capture probe sequence (duplicate spots 1 and 3) but was washed away from the negative control droplets (duplicate spots 2 and 4), clearly demonstrating the usefulness and superiority of the polyurethane-based hydrogel biochips, disclosed herein.

EXAMPLE II

Hybridization Experiment with a DNA Chip

A solution of 0.025 g polyurethane prepolymer having an isocyanate content of about 0.5 meq/g (Hypol PreMa G-50 manufactured by Hampshire Chemical Corporation) was prepared in 0.15 g acetonitrile. Next, a solution of 1 mg DNA (0.3 $\mu$M), having a hexane diamine at its 5' end and having the sequence $NH_2$—$(CH_2)_6$-$NH_2$-CATTGCTCAAAC-$CO_2H$, in 0.32 g of a 50 mM $NaHCO_3$ aqueous buffer at pH 9.15 was prepared. The DNA solution was added to the prepolymer solution and thoroughly mixed. A droplet of the resulting solution was manually spotted on a silanated glass slide using a capillary microtube. As a negative control, a hydrogel droplet containing no DNA was spotted next to the DNA-containing hydrogel droplet.

The glass slide, having the hydrogel droplets thereon, was submersed into washing buffer (10 mM sodium phosphate buffer with 0.5 M NaCl and 0.1% SDS at pH 7.0) for 30 minutes to remove organic solvents and block active sites to prevent non-specific binding of test DNA, Next, the slide was treated with 1 mg of a complementary fluorescence-labeled DNA, 3'-TAGTAACGAGTTTGCC-5'-Fluorescein, in 600 $\mu$L hybridization buffer (10 mM sodium phosphate buffer with 0.5 M NaCl and 0.1% SDS at pH 7.0) at room temperature, for 1 hour. Non-specifically bound DNA was removed by washing for two hours in washing buffer. The resulting slide was observed with a hand-held fluorescence detector (Model UVGL-25, UVP). The complimentary, test DNA diffused into the hydrogel microdroplet where it hybridized to the gel-bound DNA capture probe sequence but was washed away from the negative control droplet, demonstrating the reliability and usefulness of the present polyurethane-based hydrogel biochips in DNA hybridization assays.

The polyurethane-based biochip methods and systems described herein have been described in terms of particular embodiments of the best mode contemplated. However, it will be appreciated by those of skill in the art that certain parameters, such as the particular aprotic solvent selected, the polymerization time desired and/or used, the biomolecular probe selected for binding to the hydrogel, as well as other parameters, may be altered without departing from the nature of the invention as described herein. Thus, the scope of the invention should be determined not with reference to the above description alone but with reference to the appending claims along with their full scope of equivalents.

What is claimed is:

1. A method of preparing a biochip having an organic solvent soluble biomolecule covalently bound thereto, the method comprising:
   a) providing a solid substrate having a top surface with reactive molecules thereon;
   b) providing a solution comprising the biomolecule in an aprotic organic solvent;
   c) providing a polyurethane-based hydrogel prepolymer in an aprotic organic solvent;
   d) derivatizing the polyurethane-based hydrogel prepolymer with the biomolecule from step (b);
   e) initiating polymerization of the derivatized polyurethane-based hydrogel prepolymer of step (d) by adding a buffered aqueous solution thereto; and
   f) microspotting the polymerizing hydrogel solution of step (e) onto the top surface of the substrate of step (a), such that the polymerizing hydrogel reacts with the reactive molecules on the surface of the substrate resulting in covalent binding of the hydrogel to the substrate.

2. The method according to claim 1, wherein the step of providing a solid substrate having reactive molecules on its top surface, comprises providing a glass substrate, wherein the glass substrate has been derivatized to have active amines on its surface.

3. The method according to claim 1, wherein the step of providing a solution comprising the biomolecule in an aprotic organic solvent comprises providing a solution containing a peptide nucleic acid dissolved in an aprotic organic solvent.

4. The method according to claim 3, wherein the peptide nucleic acid is dissolved in an aprotic organic solvent selected from the group consisting of N-methyl-2-pyrrolidinone (NMP), dimethylformamide (DMF) and acetone.

5. The method according to claim 4, wherein the peptide nucleic acid is dissolved in NMP.

6. The method according to claim 1, wherein the step of providing a polyurethane-based hydrogel prepolymer in aprotic organic solvent comprises providing a solution of less than about 10% polyurethane-based hydrogel prepolymer in aprotic organic solvent.

7. The method according to claim 6, wherein the step of providing a polyurethane-based hydrogel prepolymer in aprotic organic solvent comprises providing a solution of no more than about 5% polyurethane-based hydrogel prepolymer in aprotic organic solvent.

8. The method according to claim 1, wherein the step of providing a polyurethane-based hydrogel prepolymer in aprotic organic solvent comprises providing a prepolymer of polyethyleneoxide capped with water-active diisocyanates, wherein the isocyanate-capped polyethyleneoxide is lightly cross-linked with polyols.

9. The method according to claim 8, wherein the isocyanate-capped polyethyleneoxide prepolymer contains less than about 0.8 meq/g active isocyanates.

10. The method according to claim 1, wherein the step of providing a polyurethane-based hydrogel prepolymer in aprotic organic solvent comprises providing a polyurethane-based hydrogel in an aprotic organic solvent selected from the group consisting of N-methyl-2-pyrrolidinone (NMP), dimethylformamide (DMF), acetonitrile and acetone.

11. The method according to claim 10, wherein the polyurethane-based hydrogel prepolymer is dissolved in acetonitrile.

12. The method according to claim 1, wherein derivatization of the polyurethane-based hydrogel with the biomolecule comprises reacting a solution of peptide nucleic acid in NMP with a solution of polyurethane-based hydrogel in acetonitrile.

13. The method according to claim 12, wherein the ratio of acetonitrile to NMP, in the derivatization step is selected to be between about 3:1 and about 2:1.

14. The method according to claim 1, wherein the step of initiating polymerization of the derivatized polyurethane-based hydrogel prepolymer comprises adding an aqueous solution of sodium bicarbonate buffer, to the derivatized prepolymer solution, wherein the reaction is buffered at a pH from about 7.2 to about 9.5.

15. The method according to claim 14, wherein the step of providing a polyurethane-based hydrogel prepolymer in an aprotic organic solvent comprises providing the polyurethane-based prepolymer in acetonitrile such that the polymerizing solution contains at least about 30% acetonitrile.

16. A method of preparing a biochip having a peptide nucleic acid covalently bound thereto, the method comprising:

a) providing a transparent, solid substrate having a top surface with reactive amines thereon;

b) providing a solution of peptide nucleic acid in aprotic organic solvent;

c) providing an aprotic organic solvent solution of polyurethane-based hydrogel prepolymer having active isocyanates;

d) derivatizing the hydrogel prepolymer of step (c) with the peptide nucleic acid of step (b);

e) initiating polymerization of the derivatized polyurethane-based hydrogel prepolymer of step (d), by adding an aqueous buffer solution thereto; and f) microspotting the polymerizing hydrogel solution of step (e) onto the substrate of step (a), such that active isocyanates of the polymerizing hydrogel react with the reactive amines on the surface of the substrate such that the hydrogel is covalently bound the substrate.

17. The method according to claim 16, wherein the step of providing a transparent, solid substrate comprises providing a glass substrate derivatized with an amine.

18. The method according to claim 16, wherein the step of providing an aprotic organic solvent solution of polyurethane-based hydrogel prepolymer having active isocyanates comprises providing the polyurethane-based hydrogel prepolymer in sufficient acetonitrile such that the polymerizing solution of step (e) contains at least about 30% acetonitrile.

19. The method according to claim 16, wherein the step of providing an aprotic organic solvent solution of polyurethane-based hydrogel prepolymer comprises providing an aprotic organic solvent solution of polyurethane-based hydrogel prepolymer having an active isocyanate content of at least about 0.3 meq/g.

20. The method according to claim 19, wherein the active isocyanate content of the polyurethane-based hydrogel prepolymer is between about 0.3 and 0.8 meq/g.

21. The method according to claim 20, wherein derivatization of the polyurethane-based hydrogel with the peptide nucleic acid comprises reacting a solution of peptide nucleic acid in NMP with a solution of polyurethane-based hydrogel in acetonitrile.

22. The method according to claim 21, wherein the ratio of acetonitrile to NMP, in the derivatization step, is selected to be between about 3:1 and about 2:1.

23. The method according to claim 16, wherein the derivatization step comprises derivatizing less than about 20% of the active isocyanates of the polyurethane-based hydrogel prepolymer with the peptide nucleic acid.

24. The method according to claim 23, wherein no more than about 10% of the active isocyanates of the polyurethane-based hydrogel are derivatized with the peptide nucleic acid.

25. The method according to claim 16, wherein the step of initiating polymerization of the derivatized polyurethane-based hydrogel prepolymer comprises adding an aqueous solution of sodium bicarbonate buffer, to the derivatized prepolymer solution, wherein the reaction is buffered at a pH from about 7.2 to about 9.5.

26. A method of preparing a polyurethane-based hydrogel biochip having a biomolecule immobilized thereon, the method comprising the steps of:

a) providing an organic solvent solution of a polyurethane-based hydrogel prepolymer;

b) providing a solution of a biomolecule;

c) covalently binding the biomolecule to the polyurethane-based hydrogel prepolymer;

d) initiating polymerization of the polyurethane-based hydrogel prepolymer; and e) dispensing the polymerizing polyurethane-based hydrogel prepolymer onto a solid substrate, such that said solution is covalently bound to said substrate.

27. The method according to claim 26, wherein the step of covalently binding the biomolecule to a polyurethane-based hydrogel prepolymer comprises:

a) providing a solution of polyurethane-based hydrogel prepolymer in acetonitrile, wherein the hydrogel prepolymer has an active isocyanate content of less than about 0.8 meq/g;

b) providing a solution of peptide nucleic acid in NMP, wherein the concentration of peptide nucleic acid is equal to at least about 10% of the concentration of active isocyanates in the hydrogel prepolymer solution and wherein the volume of NMP is at most about one half the volume of the acetonitrile; and c) reacting the hydrogel prepolymer solution and peptide nucleic acid solution such that less than about 20% of the active isocyanates of the hydrogel prepolymer are covalently bound to the biomolecule.

28. The method according to claim 27, wherein the step of initiating polymerization of the hydrogel prepolymer solution comprises adding an aqueous buffer solution, at a pH between about 7.2 and 9.5, to the hydrogel prepolymer solution.

29. The method according to claim 26, wherein the steps of covalently binding the biomolecule to the polyurethane-based hydrogel prepolymer and initiating polymerization of the polyurethane-based hydrogel prepolymer are performed simultaneously.

30. The method according to claim 29, wherein the step of providing a solution of a biomolecule comprises providing a biomolecule in aqueous buffer solution at a pH of about 7.2 to about 9.5.

31. The method according to claim 30, wherein the step of providing a solution of a biomolecule comprises providing an oligonucleotide in a sodium bicarbonate aqueous buffer solution at a pH of about 9.15.

32. The method according to claim 26, wherein the step of providing an organic solvent solution of a polyurethane-based hydrogel prepolymer comprises providing an acetonitrile solution of polyurethane-based hydrogel prepolymer having an active isocyanate content of less than about 0.8 meq/g.

33. The method according to claim 32, wherein the step of providing a solution of a biomolecule comprises providing a solution of a biomolecule at a concentration of less than about 20% the concentration of active isocyanates in the polyurethane-based hydrogel prepolymer.

34. The method according to claim 33, wherein the solution of biomolecule is provided at a concentration or less than about 10% the concentration of active isocyanates in the polyurethane-based hydrogel prepolymer.

35. The method according to claim 32, wherein the step of providing an acetonitrile solution of polyurethane-based hydrogel prepolymer comprises providing the polyurethane-based hydrogel prepolymer in a sufficient volume of acetonitrile such that during the step of initiating polymerization the hydrogel solution contains at least about 30% acetonitrile.

36. A polyurethane-based hydrogel biochip comprising:

a) a solid, transparent substrate having active amines on its top surface;

b) a polyurethane-based hydrogel cell covalently bound to the top surface of the substrate, wherein the hydrogel cell is at least about 30 $\mu$m thick; and c) a biomolecular probe covalently bound to and within the hydrogel cell.

37. A polyurethane-based hydrogel biochip according to claim 36, wherein the polyurethane-based hydrogel cell further comprises isocyanate groups through which the hydrogel is covalently bound to the substrate.

38. A polyurethane-based hydrogel biochip according to claim 37, wherein the biomolecular probe is covalently bound to and within the hydrogel cell through isocyanate groups of the hydrogel.

39. A polyurethane-based hydrogel biochip according to claim 38, wherein less than about 20% of the isocyanate groups of the hydrogel cell are bound to the biomolecular probe.

40. A polyurethane-based hydrogel biochip according to claim 39, wherein no more than about 10% of the isocyanate groups of the hydrogel cell are bound to the biomolecular probe.

41. A polyurethane-based hydrogel biochip according to claim 36, wherein the polyurethane-based hydrogel cell is from about 50 $\mu$m and about 100 $\mu$m thick.

\* \* \* \* \*

UNITED STATES PATENT AND TRADEMARK OFFICE
CERTIFICATE OF CORRECTION

PATENT NO. : 6,174,683 B1
DATED : January 16, 2001
INVENTOR(S) : Soonkap Hahn

It is certified that error appears in the above-identified patent and that said Letters Patent is hereby corrected as shown below:

<u>Title page,</u>
Section [75] Inventors, delete "Roberto Fagnani, La Jolla, both".

Signed and Sealed this

Second Day of October, 2001

Attest:

NICHOLAS P. GODICI
Attesting Officer    *Acting Director of the United States Patent and Trademark Office*